(12) United States Patent
Lu et al.

(10) Patent No.: US 8,592,755 B2
(45) Date of Patent: Nov. 26, 2013

(54) METHOD OF SWITCHING PORTS OF A SWITCHING VALVE OF A GAS CHROMATOGRAPHY-MASS SPECTROMETRY APPARATUS

(75) Inventors: Hongliang Lu, Xiamen (CN); Kai Lin, Xiamen (CN); Jing Yu, Xiamen (CN); Feng Zhang, Xiamen (CN)

(73) Assignee: China Tobacco Fujian Industrial Co., Ltd., Xiamen (CN)

(*) Notice: Subject to any disclaimer, the term of this patent is extended or adjusted under 35 U.S.C. 154(b) by 0 days.

(21) Appl. No.: 13/609,301

(22) Filed: Sep. 11, 2012

(65) Prior Publication Data

US 2013/0126720 A1 May 23, 2013

(30) Foreign Application Priority Data

Nov. 23, 2011 (CN) .......................... 2011 1 0378205

(51) Int. Cl.
*H01J 49/04* (2006.01)
(52) U.S. Cl.
USPC ............ 250/282; 250/281; 250/288; 73/23.2; 73/23.35; 73/23.37; 73/23.41; 73/23.42

(58) Field of Classification Search
USPC .............. 250/281, 282, 288; 73/23.35, 23.37, 73/23.41, 23.42, 23.2, 23.22, 61.52
See application file for complete search history.

(56) References Cited

U.S. PATENT DOCUMENTS

| | | | | |
|---|---|---|---|---|
| 5,492,555 | A * | 2/1996 | Strunk et al. ...................... | 95/86 |
| 5,720,798 | A * | 2/1998 | Nickerson et al. ............... | 96/102 |
| 2004/0232366 | A1* | 11/2004 | Seeley ............................ | 251/12 |
| 2007/0271997 | A1* | 11/2007 | O'Brien ....................... | 73/23.37 |
| 2010/0206045 | A1* | 8/2010 | Fisher .......................... | 73/23.42 |
| 2011/0186731 | A1* | 8/2011 | Van Els et al. ................ | 250/288 |
| 2013/0134095 | A1* | 5/2013 | Anderer et al. ............... | 210/656 |

* cited by examiner

*Primary Examiner* — Michael Logie

(57) ABSTRACT

A method of operating a switching valve of a GC-MS apparatus is provided with installing a sample injector; connecting a first capillary column downstream of the sample injector; installing a heart-cutting unit downstream of the first capillary column; installing a first interconnecting column and a second capillary column to the heart-cutting unit respectively; connecting a switching valve to the heart-cutting unit via a first interconnecting column and a second capillary column respectively wherein the switching valve includes a plurality of ports; connecting the switching valve to an MS via a second interconnecting column; and switching ports to create different sample loops for passing compounds from the heart-cutting unit to the MS or passing compounds from the heart-cutting unit to the discharge column to be purged.

3 Claims, 7 Drawing Sheets

METHOD OF SWITCHING PORTS OF A SWITCHING VALVE OF A GAS CHROMATOGRAPHY-MASS SPECTROMETRY APPARATUS

BACKGROUND OF THE INVENTION

1. Field of the Invention

The invention relates to gas chromatography-mass spectrometry (GC-MS) instrument and more particularly to a method of switching ports of a switching valve of a GC-MS apparatus.

2. Description of Related Art

A conventional gas chromatography-mass spectrometry (GC-MS) apparatus is shown in FIG. 1 and comprises a sample injector 1, a heart-cutting unit 3 for separating gaseous compounds carried by carrier gas from the sample injector 1 into different fractions, a first capillary column 2 interconnecting the sample injector 1 and the heart-cutting unit 3, a flame ionization detector (FID) 7, an interconnecting column 4 interconnecting the FID 7 and the heart-cutting unit 3, a mass spectrometer (MS) 6, and a second capillary column 5 interconnecting the heart-cutting unit 3 and the MS 6. The FID 7 can be replaced with nitrogen-phosphorous detector (NPD) or one of similar detectors.

However, a number of drawbacks have been found in the conventional GC-MS apparatus. In detail, as sample gaseous compounds are preliminarily separated by the first capillary column 2 into different fractions, through setting different time slot and carrier gas pressure of the heart-cutting unit 3, the simple compounds with good separation separated by the first capillary column 2 are to be sent to a detector such as FID or NPD via the interconnecting column 4 for analysis while the complex compounds which are not separated from each other completely and cannot be further separated from each other by the first capillary column 2, are required to be sent to the second capillary column 5, which are of different solid phase from that of the first capillary column 2, for further separation before being sent to the MS 6 for quantitative and qualitative analysis. The simple compounds detected by the detector FID or NPD from a conventional GC-MS will only be able to be resulted in a quantitative analysis while no qualitative analysis as regards the name, structure, CAS No., etc. of such simple compounds may be concluded, thus causing inconvenience to the user. That is, different fractions cannot be sent to the MS 6 at the same time for analysis. Adding another MS to the GC-MS device can solve the problem but it will increase cost. Further, relevant software is required for control purposes.

Thus, the need for improvement still exists.

SUMMARY OF THE INVENTION

It is therefore one object of the invention to provide a method of operating a switching valve of a GC-MS apparatus, comprising the steps of installing a sample injector; installing a heart-cutting unit downstream of the sample injector; connecting a first capillary column to the sample injector and the heart-cutting unit; connecting a second capillary column downstream to the heart-cutting unit; connecting a switching valve downstream to the heart-cutting unit via a first interconnecting column; connecting the switching valve downstream to the heart-cutting unit via the second capillary column wherein the switching valve includes a plurality of ports; connecting the switching valve to a mass spectrometer (MS) via a second interconnecting column; and either (a) switching at least two of the ports to create a first sample loop for passing compounds from the first capillary column to the MS via the first interconnecting column, the first sample loop, and the second interconnecting column, and (b) switching the remaining ports to create a second sample loop for passing compounds from the second capillary column to the discharge column and the second sample loop; or (c) switching at least two of the ports to create a third sample loop for passing compounds from the second capillary column to the MS via the third sample loop and the second interconnecting column, and (d) switching the remaining ports to create a fourth sample loop for passing compounds from the first capillary column to a discharge column via the first interconnecting column and the fourth sample loop.

The above and other objects, features and advantages of the invention will become apparent from the following detailed description taken with the accompanying drawings.

DETAILED DESCRIPTION OF THE INVENTION

Referring to FIGS. 2 to 7, a GC-MS apparatus in accordance with the invention comprises the following components as discussed in detail below.

A sample injector 10 is provided to allow carrier gas to pass through to carry chemical compounds. A heart-cutting unit 30 is provided to separate the gaseous compounds, carried by the carrier gas from the sample injector 10 and preliminarily separated by the first capillary column 20, into different fractions which are to be further sent to a first interconnecting column 40 and a second capillary column 50 respectively. A first interconnecting column 40 interconnects the heart-cutting unit 30 and the switching valve 60 (e.g., 6-port switching valve). A second capillary column 50 interconnects the heart-cutting unit 30 and the switching valve 60. A second interconnecting column 70 interconnects the switching valve 60 and a mass spectrometer (MS) 80.

The switching valve 60 as the subject of the invention comprises first, second, third, fourth, fifth and sixth ports 61, 62, 63, 64, 65 and 66. The first interconnecting column 40 is connected to one of the ports, the second capillary column 50 is connected to another one of the ports, a discharge column 90 is connected to still another one of the ports, and the third interconnecting column 70 is connected to further another one of the ports as detailed below.

Figure 1:
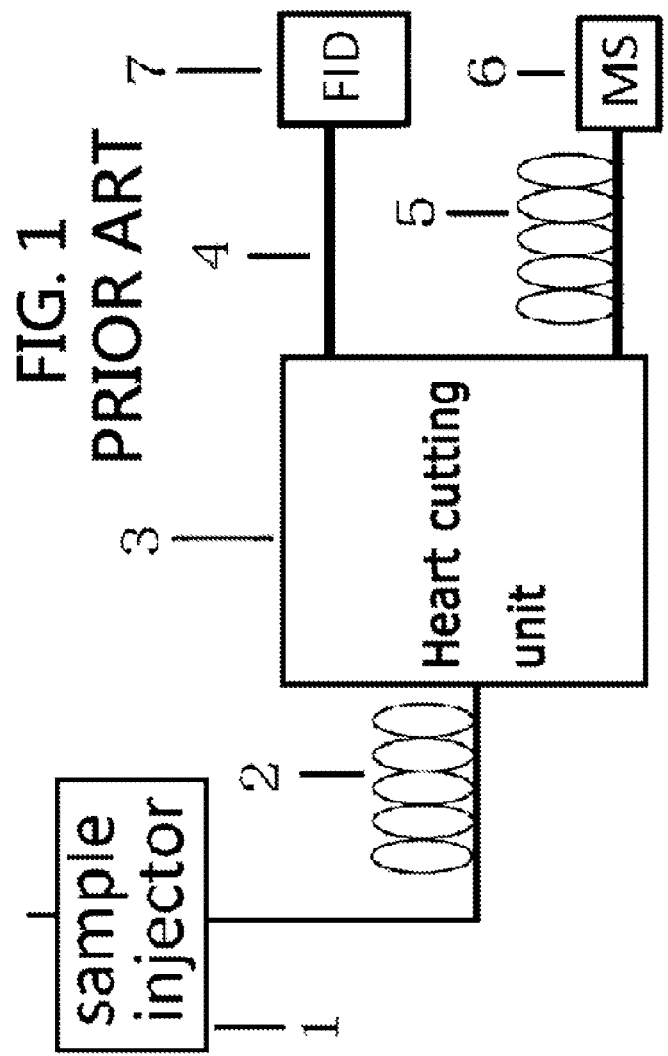
FIG. 1 is a schematic diagram of a conventional GC-MS apparatus.
Figure 2:
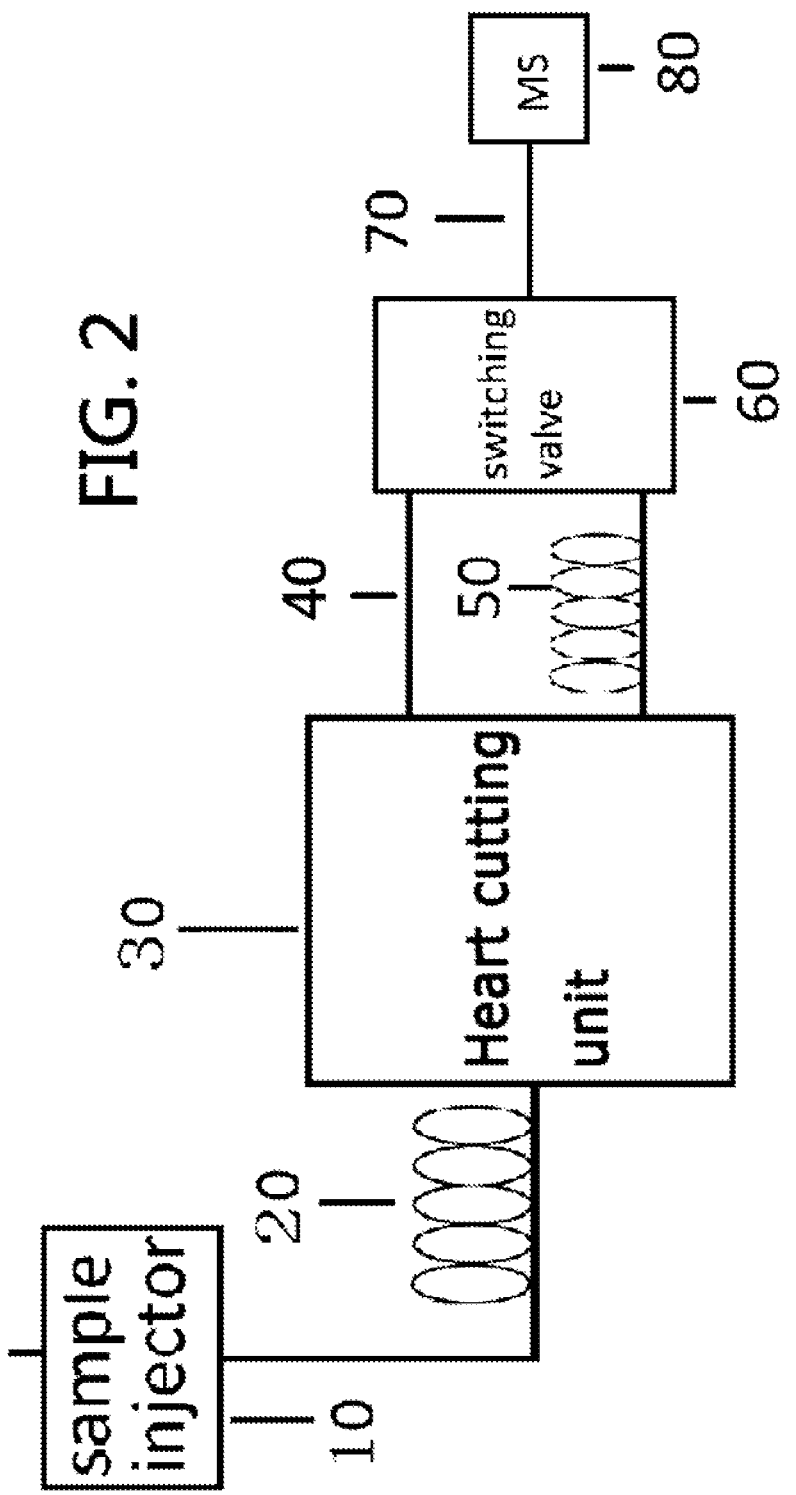
FIG. 2 is a schematic diagram of a GC-MS apparatus according to the invention.
Figure 3:
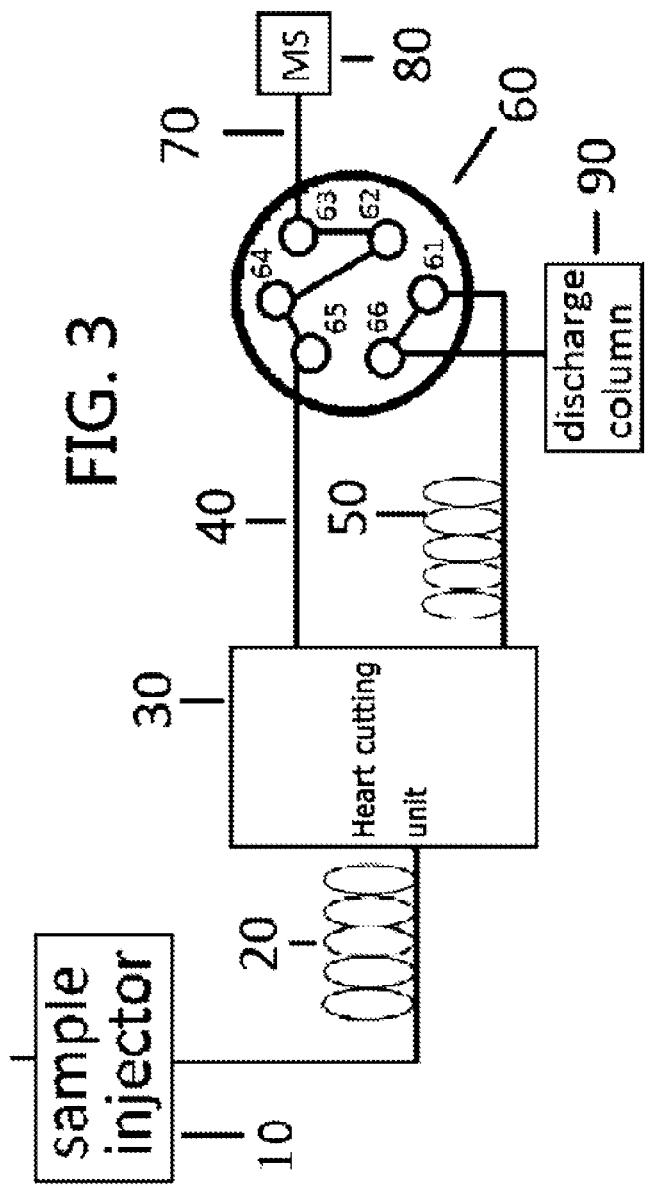
FIG. 3 is a view similar to FIG. 2 with the switching valve being shown in details in its first configuration.
Figure 4:
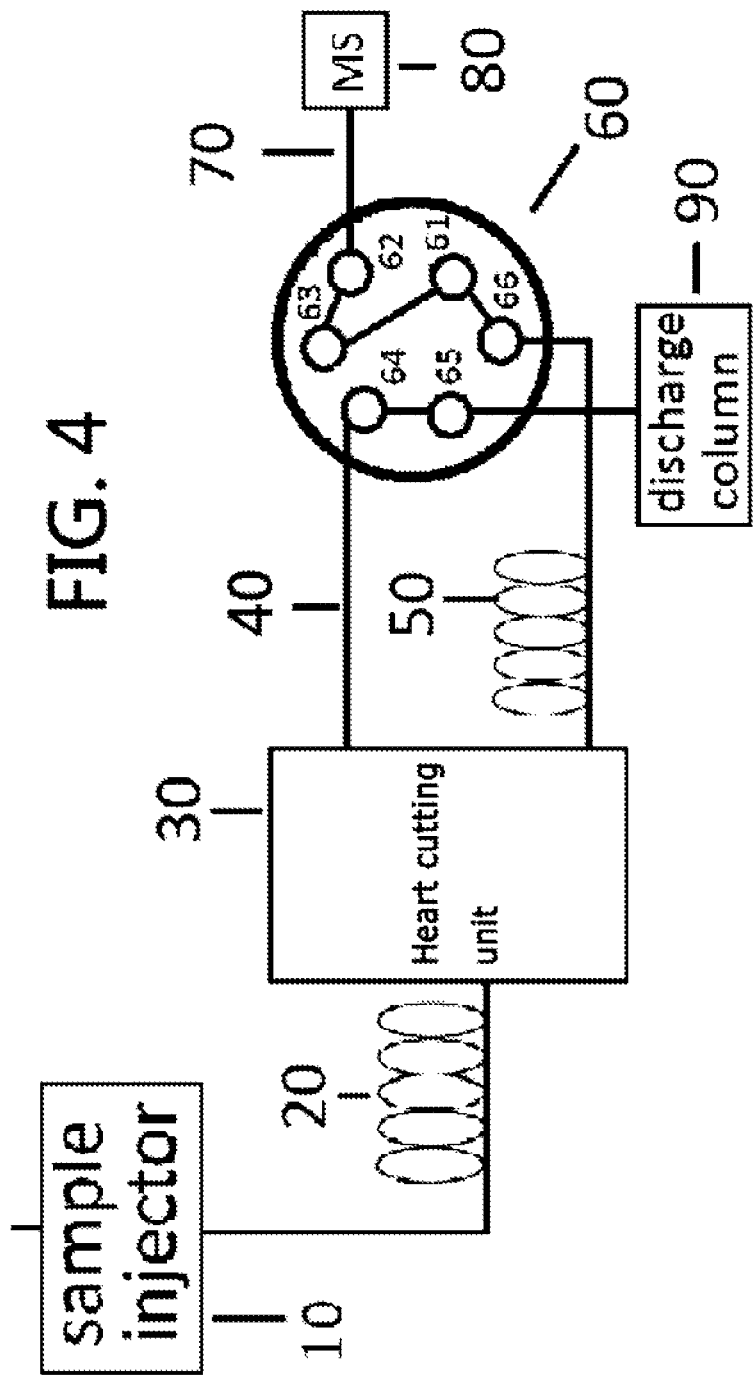
FIG. 4 is a view similar to FIG. 3 showing a second configuration of the switching valve.

For introducing components of the chemical compounds separated from the heart cutting unit 30 (i.e. the first and the second vaporized compounds) to the MS 80, an individual may set the retention time and carrier gas pressure of the heart-cutting unit 30 and rotate the switching valve 60 to switch ports into a configuration as shown either in FIG. 3 or in FIG. 4.

In FIG. 3, a first sample loop consisting of the fifth, fourth, second, and third ports 65, 64, 62, and 63 is created in the switching valve 60. As a result, the first vaporized compounds may travel from the first interconnecting column 40 to the MS 80 for analysis via the first sample loop and the second interconnecting column 70. Moreover, the second vaporized compounds may travel from the second capillary column 50 to the discharge column 90 to be purged from the GC-MS apparatus via a second sample loop consisting of the first and sixth ports 61 and 66.

In FIG. 4, an individual may rotate the switching valve 60 to switch ports into a configuration as shown. A third sample loop consisting of the sixth, first, third, and second ports 66, 61, 63, and 62 is created in the switching valve 60. As a result, the second vaporized compounds may travel from the second capillary column 50 to the MS 80 for analysis via the third sample loop and the second interconnecting column 70. Moreover, the first vaporized compounds may travel to the discharge column 90 to be purged from the GC-MS apparatus via the first interconnecting column 40 and a fourth sample loop consisting of the fourth and fifth ports 64 and 65.

Figure 5:
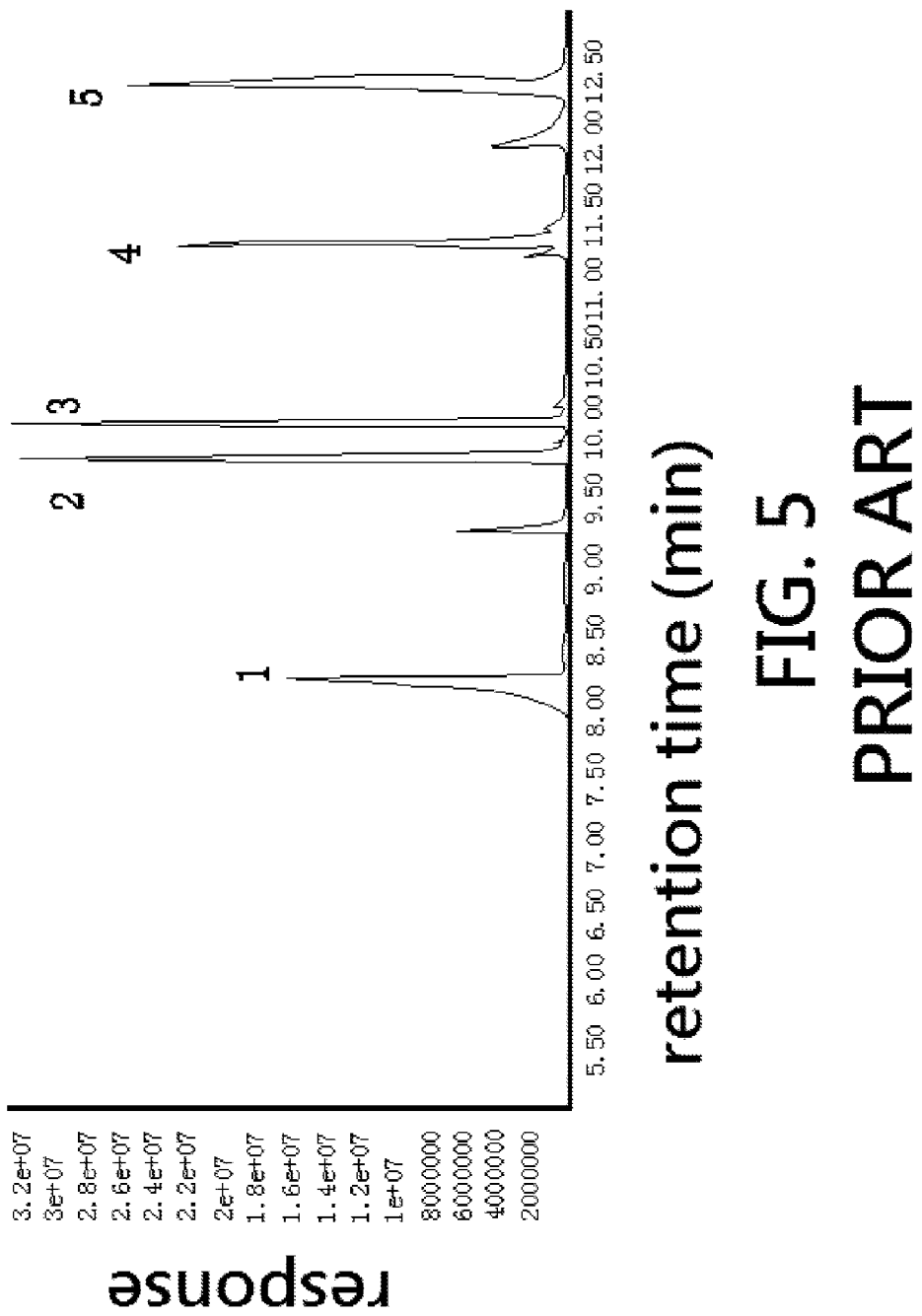
FIG. 5 is a chromatogram depicting retention time versus response of five distinct peaks of separated components of chemical compounds according to the conventional GC-MS apparatus which is not equipped with a switching valve.

Referring to FIG. 5, it is a chromatogram depicting retention time versus response (i.e., base peak intensity) of five distinct peaks (i.e., labeled 1, 2, 3, 4 and 5) of separated components of chemical compounds according to the conventional GC-MS apparatus. However, its retention time is short (e.g., first peak having a retention time of 7.90-8.30 minutes, second peak having a retention time of 9.72-9.90 minutes, third peak having a retention time of 9.98-10.10 minutes, fourth peak having a retention time of 11.24-11.60 minutes, and fifth peak having a retention time of 12.30-12.60 minutes) and its responses are not strong.

Figure 6:
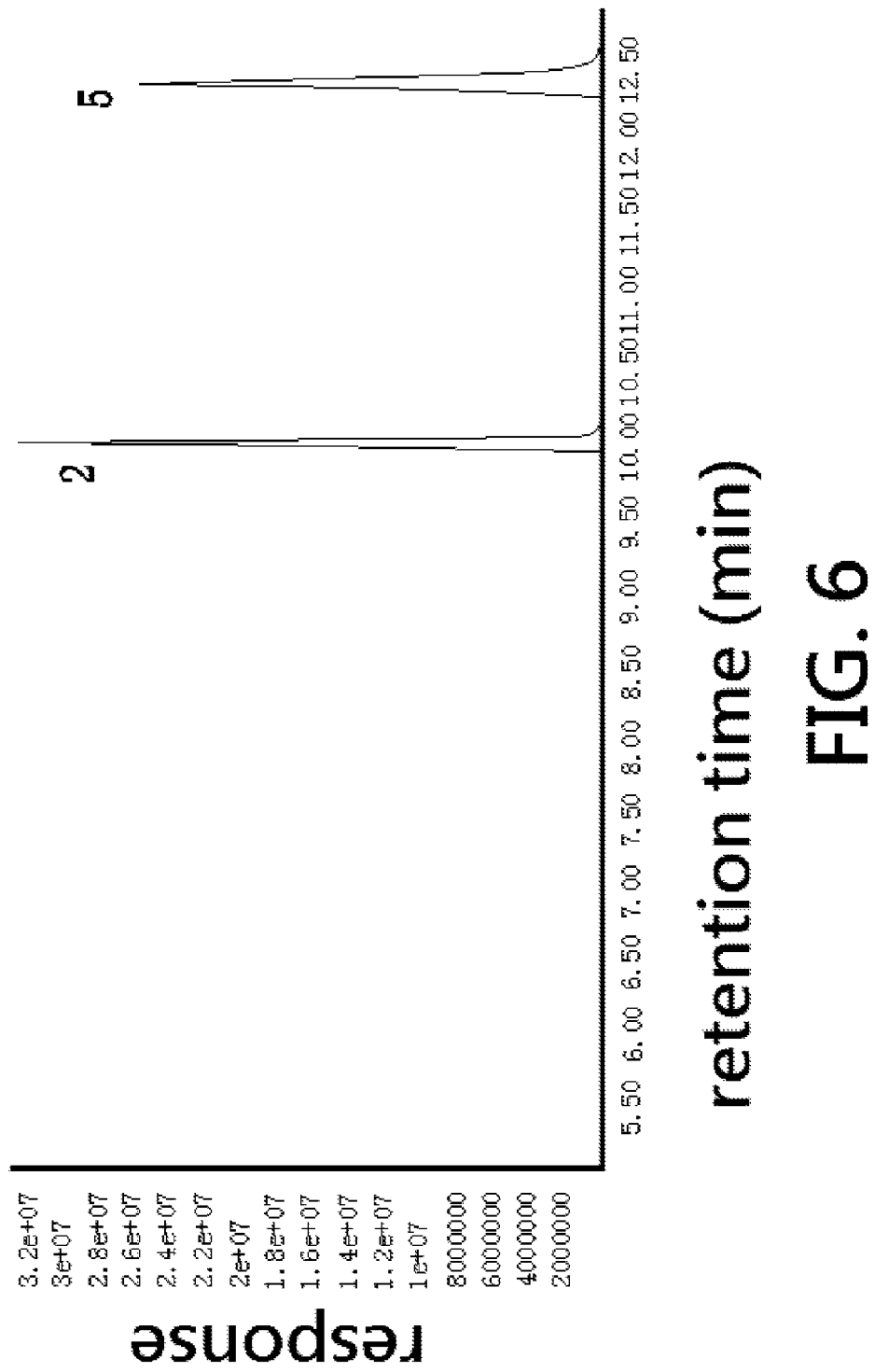
FIG. 6 is a chromatogram depicting retention time versus response of two distinct peaks of separated components of chemical compounds according to the GC-MS apparatus of the invention, the components of chemical compounds being from the second capillary column after further separation and sending to the MS via the switching valve and the second interconnecting column.

As shown in the chromatogram of FIG. 6, two distinct peaks of separated components of chemical compounds (i.e., labeled 2 and 5) according to the GC-MS apparatus of the invention are shown in which the second vaporized compounds from the first capillary column 20 are sent to the MS 80 via the second capillary column 50, the switching valve 60 and the second interconnecting column 70.

Figure 7:
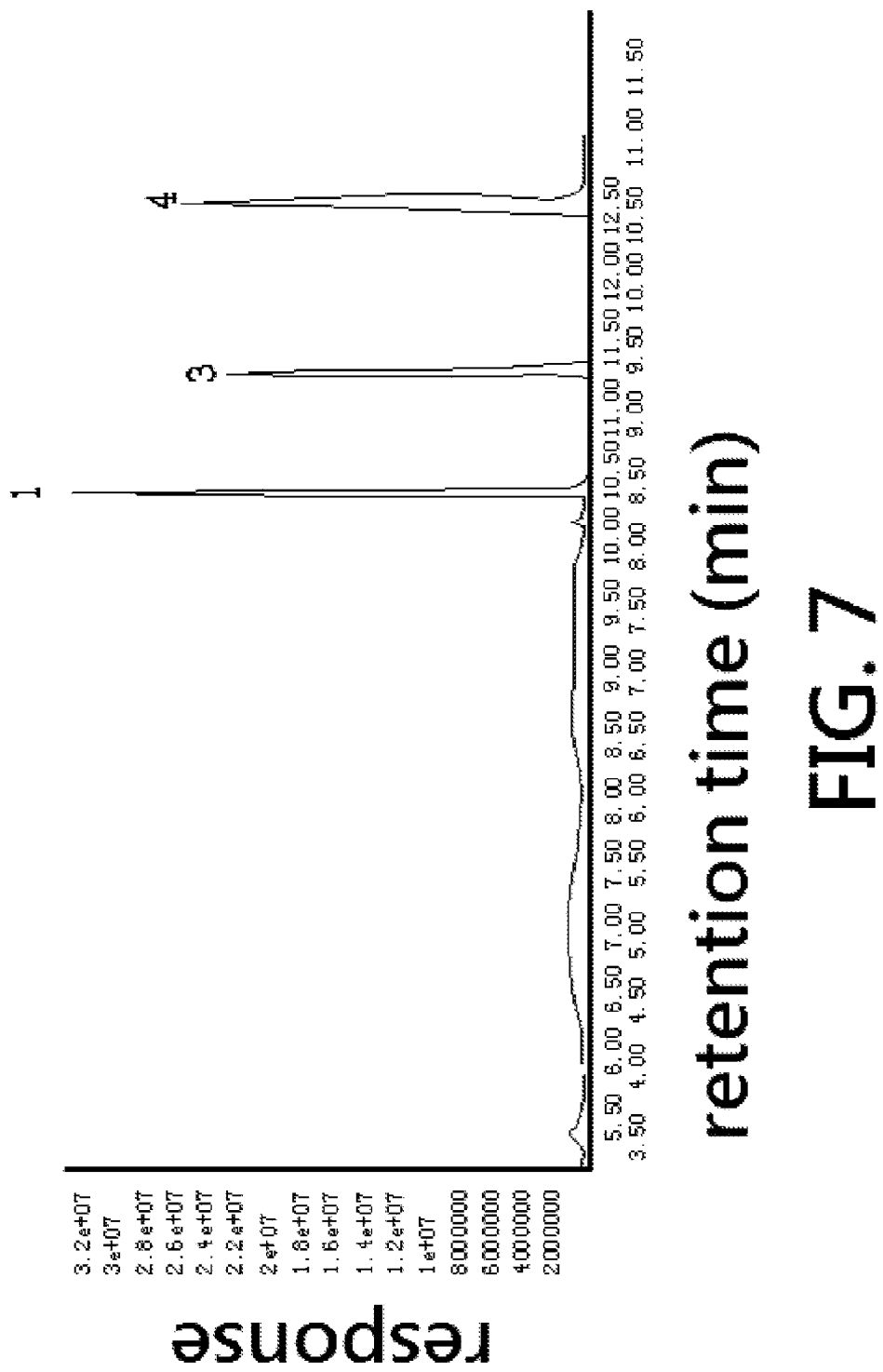
FIG. 7 is a chromatogram depicting retention time versus response of three distinct peaks of separated components of chemical compounds according to the GC-MS apparatus of the invention, the components of chemical compounds being from the first capillary column and sending to the MS via the first interconnecting column, the switching valve, and the second interconnecting column.

As shown in the chromatogram of FIG. 7, three distinct peaks of finely separated components of chemical compounds (i.e., labeled 1, 3 and 4) according to the GC-MS apparatus of the invention are shown in which the first vaporized compounds from the first capillary column 20 are sent to the MS 80 via the first interconnecting column 40, the switching valve 60, and the second interconnecting column 70.

As a comparison with the conventional chromatogram of FIG. 5, it is found that retention time is increased and response is stronger according to the GC-MS apparatus of the invention.

Above can be further ascertained by the following two experiments:

Experiment I

For introducing components of the chemical compounds (i.e., labeled 2 and 5) into the second capillary column 50 for further separation, an individual may set the retention time of the heart-cutting unit to cut the components consisting the compounds labeled 2 and rotate the switching valve 60 at the time of 9.5 minutes to switch ports into a configuration as shown in FIG. 4 for introducing the compounds labeled 2 into GC-MS 80 via the second capillary column 50; and then set the retention time of the heart-cutting unit to turn off channel between the heart-cutting unit and the second capillary column 50 at the time of 10.5 minutes but the still maintain the configuration of the ports of the switching valve as shown in FIG. 4. Further, for introducing components of the compounds labeled 5 into the second capillary column 50 for further separation, an individual may first set the retention time of the heart-cutting unit to cut the components consisting the compounds labeled 5 and rotate the switching valve 60 at the time of 12.2 minutes to switch ports into a configuration as shown in FIG. 4 for introducing the compounds labeled 5 into GC-MS 80 via the second capillary column 50; and then set the retention time of the heart-cutting unit to turn off channel between the heart-cutting unit and the second capillary column 50 at the time of 13.0 minutes but the still maintain the configuration of the ports of the switching valve as shown in FIG. 4.

As a result, components of the chemical compounds (i.e., labeled 2 and 5) can be introduced into the second capillary column 50. Thereafter, the separated components of the chemical compounds labeled 2 and 5 may travel from the second capillary column 50 to the MS 80 for analysis via the third sample loop consisting of the sixth, first, third and second ports 66, 61, 63, and 62 in the switching valve 60 and the second interconnecting column 70. Moreover, the components of the chemical compounds separated from the first capillary column 20 (i.e., labeled 1, 3 and 4 in FIG. 5) may travel to the discharge column 90 to be purged from the GC-MS apparatus via the first interconnecting column 40 and the fourth sample loop consisting of the fourth and fifth ports 64 and 65.

Experiment II

For introducing components of the chemical compounds (i.e., labeled 1, 3 and 4 in FIG. 5) separated from the first capillary column 20 to the MS 80 directly, an individual may set the retention time of the heart-cutting unit to cut the components consisting the compounds labeled 1 and rotate the switching valve 60 to switch ports into a configuration as shown in FIG. 3 at the time of 7.5 minutes for introducing the compound labeled 1 into GC-MS 80 via the first interconnecting column 40; and then set the retention time of the heart-cutting unit to turn off channel between the heart-cutting unit and the first interconnecting column 40 at the time of 8.5 minutes but the still maintain the configuration of the ports of the switching valve as shown in FIG. 3. Further, For introducing components of the compounds labeled 3 and 4 to the MS 80, an individual may first set the retention time of the heart-cutting unit to cut the components consisting the compounds labeled 3 and 4 and rotate the switching valve 60 to switch ports into a configuration as shown in FIG. 3 at the time of 9.95 minutes for introducing the compound labeled 3 and 4 into GC-MS 80 via the first interconnecting column 40 and the second interconnecting column 70; and then set the retention time of the heart-cutting unit to turn off channel between the heart-cutting unit and the first interconnecting column 40 at time of 12.0 minutes but the still maintain the configuration of the ports of the switching valve as shown in FIG. 3.

As a result, components of the chemical compounds (i.e., labeled 1, 3 and 4) can be introduced into the first interconnecting column 40. Thereafter, the separated components of the chemical compounds may travel from the first interconnecting column 40 to the MS 80 for analysis via the second interconnecting column 70 and the first sample loop consisting of the fifth, fourth, second and third ports 65, 64, 62, and 63 in the switching valve 60 (see FIG. 3). Moreover, the components of the chemical compounds separated from the first capillary column 20 (i.e., labeled 2 and 5) may travel to the discharge column 90 to be purged from the GC-MS apparatus via the second capillary column 50 and the second sample loop consisting of the first and sixth ports 61 and 66.

By injecting the same complex sample twice into the injector and performing the steps as stated in Experiment I and Experiment II, full quantitative and qualitative information such as the name, structure, CAS No., etc. may be concluded for such complex sample.

It is found that co-eluting interferences in the chromatogram according to the conventional GC-MS apparatus (see FIG. 5) have been greatly eliminated by the invention when comparing with the chromatogram according to the GC-MS apparatus of the invention in either FIG. 6 or FIG. 7. As a result, a more accurate analysis can be made by the invention.

While the invention has been described in terms of preferred embodiments, those skilled in the art will recognize that the invention can be practiced with modifications within the spirit and scope of the appended claims.

What is claimed is:

1. A method of operating a switching valve of a gas chromatography-mass spectrometry (GC-MS) apparatus, comprising the steps of:
   (1) installing a sample injector;
   (2) installing a heart-cutting unit downstream of the sample injector;
   (3) connecting a first capillary column to the heart-cutting unit and a second capillary column to the heart-cutting unit respectively;
   (4) connecting a switching valve to the heart-cutting unit via a first interconnecting column and connecting the switching valve to the heart-cutting unit via a second capillary column respectively wherein the switching valve includes a plurality of ports;
   (5) connecting the switching valve to a mass spectrometer (MS) via a second interconnecting column; and
   (6) either (a) switching at least two of the ports to create a first sample loop for passing compounds from the first capillary column to the MS via the first interconnecting column, the first sample loop, and the second interconnecting column, and (b) switching the remaining ports to create a second sample loop for passing compounds from the second capillary column to the discharge column via the second capillary column and the second sample loop; or
   (c) switching at least two of the ports to create a third sample loop for passing compounds from the second capillary column to the MS via the third sample loop and the second interconnecting column, and (d) switching the remaining ports to create a fourth sample loop for passing compounds from the first capillary column to a discharge column via the first interconnecting column and the fourth sample loop.

2. The method of claim 1, wherein the compounds from the second capillary column pass the third sample loop and the second interconnecting column to arrive at the MS for analysis.

3. The method of claim 1, wherein step (6) is performed twice repeatedly.

\* \* \* \* \*